United States Patent [19]

Masch

[11] Patent Number: 4,728,319

[45] Date of Patent: * Mar. 1, 1988

[54] INTRAVASCULAR CATHETER

[76] Inventor: Helmut Masch, 764 Asbury St., San Jose, Calif. 95126

[*] Notice: The portion of the term of this patent subsequent to Sep. 29, 2004 has been disclaimed.

[21] Appl. No.: 865,962

[22] Filed: May 21, 1986

Related U.S. Application Data

[63] Continuation-in-part of Ser. No. 841,879, Mar. 20, 1986, Pat. No. 4,696,667.

[51] Int. Cl.⁴ .............................................. A61B 17/20
[52] U.S. Cl. .......................................... 604/22; 604/43; 604/267; 128/304; 128/305; 128/772
[58] Field of Search ........................ 604/22, 27, 35, 43, 604/53, 266, 267; 128/305, 305.1, 311, 318, 751–758, 304, 772, 303 R, 312, 319, 328, 348.1; 30/204, 205, 240; 15/104.3 SN

[56] References Cited

U.S. PATENT DOCUMENTS

| 3,320,957 | 5/1967 | Sokolik | 128/311 |
| 3,614,953 | 10/1971 | Moss | 128/305.1 |
| 3,732,858 | 5/1973 | Banko | 604/267 |
| 3,844,272 | 10/1974 | Banko | 128/305 |
| 4,299,226 | 11/1981 | Banka | 604/53 |
| 4,631,052 | 12/1986 | Kensey | 604/22 |
| 4,649,919 | 3/1987 | Thimsen et al. | 128/305 |

FOREIGN PATENT DOCUMENTS

| 2804015 | 8/1979 | Fed. Rep. of Germany | 128/305 |
| 1069398 | 5/1967 | United Kingdom | 128/751 |
| 2151929 | 7/1985 | United Kingdom | 128/305 |

*Primary Examiner*—C. Fred Rosenbaum
*Assistant Examiner*—Mario Costantino
*Attorney, Agent, or Firm*—Phillips, Moore, Lempio & Finley

[57] ABSTRACT

An intravascular catheter includes a flexible guide wire mounted for relative rotational and reciprocal movements within a reciprocal and flexible first tube. A rotary and flexible second tube is mounted on the first tube to define an annular passage therebetween and has a rotary inner cutting head secured on a distal end thereof. The inner cutting head is closely fitted within an outer cutting head that is secured on the first tube. The cutting heads are adapted to cut a blockage in a blood vessel into fragments in response to rotation of the second tube and inner cutting head. The fragments are flushed-out from the inner cutting head and are conveyed away from the cutting heads and through the annular passage by facing spiral threads defined on the first and second tubes.

18 Claims, 7 Drawing Figures

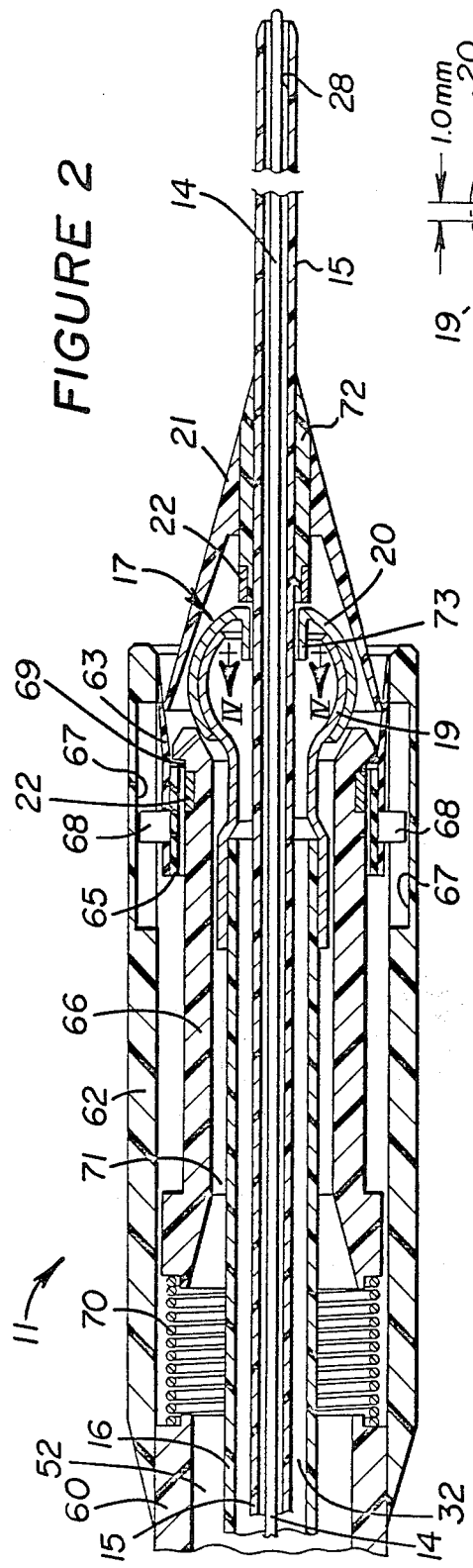
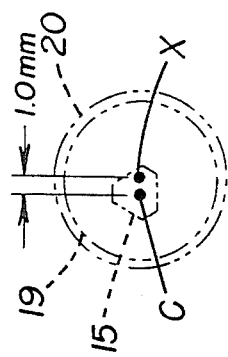
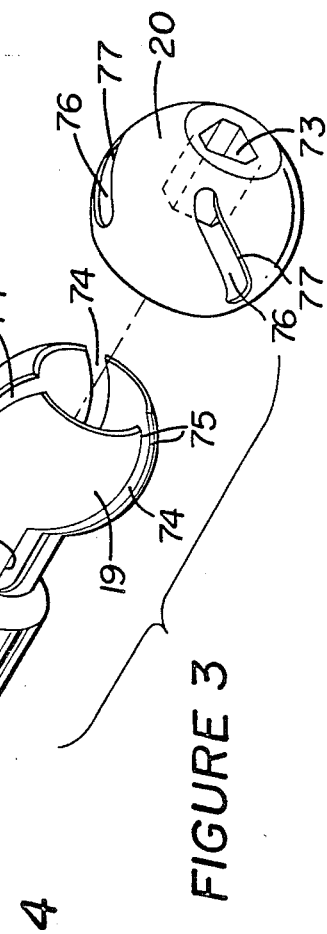
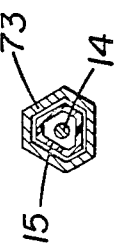

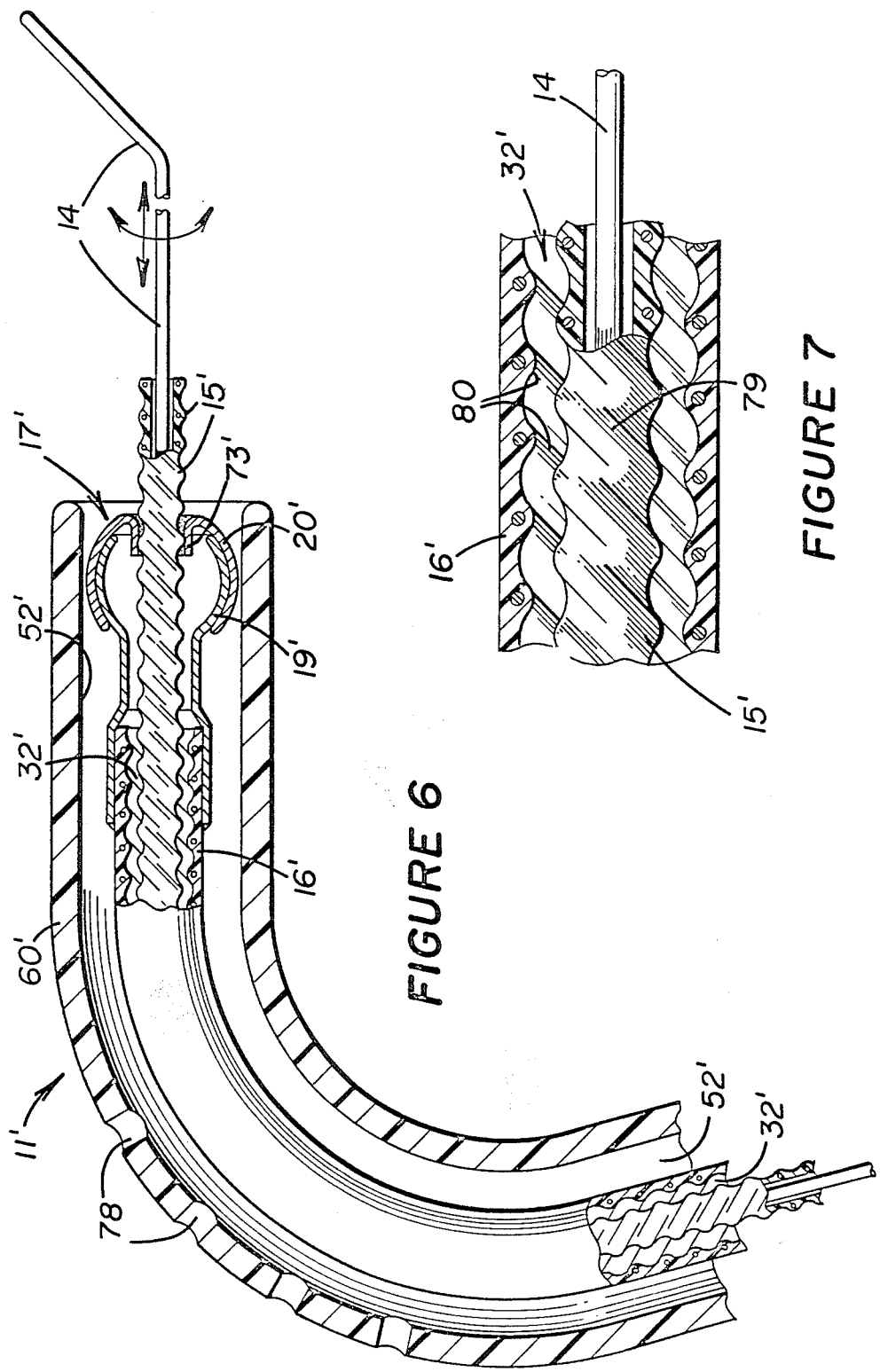

INTRAVASCULAR CATHETER

CROSS-REFERENCE TO RELATED APPLICATION

This application is a continuation-in-part of U.S. patent application Ser. No. 841,879, filed on Mar. 20, 1986, for "Intravascular Catheter and Method", now U.S. Pat. No. 4,676,667.

TECHNICAL FIELD

This invention relates to an improved medical device for surgically cleaning blood vessels and more particularly to a catheter adapted to be inserted into a blood vessel to cut a blockage therein into particles to restore the vessel to its normal or near normal condition.

BACKGROUND OF THE INVENTION

Coronary arteries carry blood to the muscles of the heart. Any blockage occurring in these arteries, such as by cholesterol build-up, calcific plaque or by clotting, can give rise to serious heart disease. In particular, when the blood supply to a part of the heart is completely cut-off, the affected area of the heart muscle may cease to function.

Medical procedures and therapy for clearing blockages of this type have included the use of chemicals to dissolve the blockage, conventional bypass surgery, laser techniques to fragment and remove the blockage, and mechanical devices to clear or compress the blockage. Such conventional procedures each has obvious limitations and inherent dangers associated with its use.

My parent U.S. patent application Ser. No. 841,879, incorporated by reference herein, discloses an intravascular catheter for clearing blocked blood vessels by engaging a blockage with a rotary cutter and flushing-out cut fragments of the blockage. This application is drawn to an alternate form of such catheter, having a reduced number of component parts.

SUMMARY OF THE INVENTION

An object of this invention is to provide an improved intravascular catheter and method for clearing blocked blood vessels efficiently, economically and safely. The catheter utilizes the same basic principles disclosed and claimed in my parent application.

The catheter of this invention also comprises rotary cutting means for engaging and cutting the blockage in the vessel into fragments. In one aspect of this invention, a flexible first tube, adapted to have a guide wire mounted therein to locate the vessel, is mounted within a rotary flexible second tube to define a passage therebetween. The cutting means is secured to the second tube for rotating into engagement with the blockage in response to rotation of the second tube. Conveying means, preferably in the form of facing spiral threads of opposite hand formed on the tubes, functions to move the fragments away from the cutting means and through the passage in response to rotation of the second tube.

In another aspect of this invention, the cutting means comprises an outer cutting head secured on the first tube and an inner cutting head secured on the second tube and rotatably mounted within the outer cutting head.

BRIEF DESCRIPTION OF THE DRAWINGS

Other objects and advantages of this invention will become apparent from the following description and accompanying drawing wherein:

FIG. 2 is an enlarged view similar to FIG. 1, but illustrates a catheter of the assembly in its retracted condition;

FIG. 3 is an enlarged exploded view of inner and outer cutting heads of the catheter;

FIG. 4 is a cross-sectional view, taken in the direction of arrows IV—IV in FIG. 2;

FIG. 5 illustrates an alternate eccentric mounting arrangement for the cutting heads;

FIG. 6 is a view similar to FIG. 2, but illustrates a alternate form of the catheter; and FIG. 7 is an enlarged sectional view, taken within circle VII—VIII in FIG. 6.

BEST MODE OF CARRYING OUT THE INVENTION

GENERAL DESCRIPTION

Figure 1:
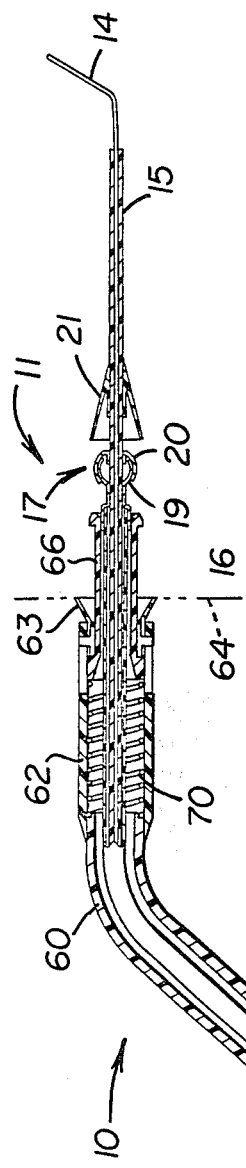
FIG. 1 illustrates the catheter assembly disclosed in my parent application.
Figure 1:
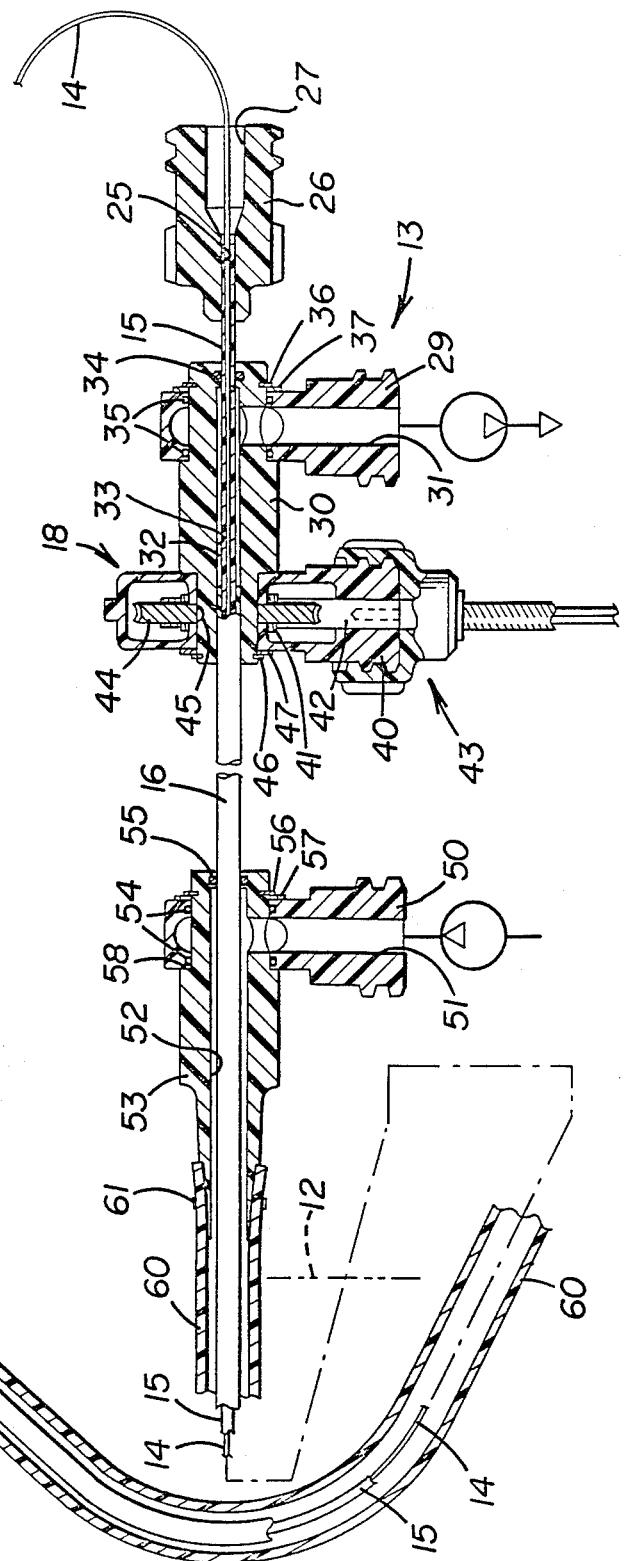

FIG. 1 illustrates a catheter assembly 10, including a catheter 11 adapted to be inserted percutaneously through the skin 12 of a patient and an operator-controlled assembly 13 positioned outside the skin. The illustrated assembly in FIG. 1 has been enlarged approximately five times over an actual assembly for clarification purposes (FIG. 2 is approximately 10:1). The catheter is adapted to be inserted into the femoral artery and abdominal aorta of a patient or into the abdominal aorta directly, through an incision made in the patient in a conventional manner. A flexible guide wire 14 is rotatably and reciprocally mounted in catheter 11 to guide the catheter through the aorta for purposes of locating a coronary artery.

A flexible first tube or sheath 15 has guide wire 14 reciprocally and rotatably mounted therein to project from a distal end thereof. The first tube is mounted in a flexible second tube 16 for simultaneous reciprocal movement therewith, but for permitting the second tube to rotate relative thereto. A cutting means 17 is adapted to engage and cut a blockage in the coronary artery into fragments in response to rotation of second tube 16, driven by a drive assembly 18 described in detail hereinafter. The blockage may be the result of cholesterol build-up, plaque, blood clots or the like.

As shown in FIGS. 2 and 3, cutting means 17 comprises a generally spherically shaped inner or male cutting head 19 secured on an end of second tube 16 for simultaneous rotation therewith and a spherically shaped outer or female cutting head 20 mounted for reciprocal movements on first tube 15. As described more fully hereinafter, cutting heads 19 and 20 have overlying blades formed thereon for engaging and cutting the blockage in the artery into fragments in much the same manner that a rotary type razor functions to shave a man's whiskers.

In carrying forth the method, the blockage in the coronary artery of a patient is precisely located and marked using conventional X-ray techniques. Catheter 11 is then inserted into the aorta of the patient with guide wire 14 being utilized to locate the blocked coronary artery and guide the catheter therein. Guide wire can be reciprocated and twisted within tube 15 for this purpose.

A conically shaped strainer cup and seal 21 is secured on tube 15 and spaced bands of a standard magnetic material 22 are suitably formed on the catheter whereby location of the bands relative to the blockage in the coronary artery can be readily detected by conventional X-ray equipment or fluroscopy techniques. Alternatively, visualization of the straining cup or other components of the catheter can be achieved by fluroscopy using the guide wire and/or a radio opaque portion of applicable components of the catheter for detection purposes. The flexible cup is pushed through the blockage and expands automatically to seal-off the downstream side of the coronary artery, relative to the blockage. Simultaneously, the catheter will expand to its extended position, illustrated in FIG. 1. The cup is composed of a material that is sufficiently porous to allow an oxygen-enriched fluid, such as a suitable fluro carbon or blood plasma, to pass through the cup to reach the heart.

Cutting means 17 is then reciprocated on tube 15 to engage the cutting means with the blockage to cut it into fragments. As described more fully hereinafter, the oxygen-enriched fluid that is pumped into cup 21 to supply the heart muscles with their needed nourishment, also functions to flush-out the cut fragments. Although this invention is particularly useful for fragmenting and cleaning-out blockages in coronary arteries, it should be understood that it has other medical and therapeutic applications, such as the cleaning out of veins.

As described hereinafter, the alternate catheter embodiment illustrated in FIGS. 6 and 7 is used in a similar manner.

DETAILED DESCRIPTION (FIGS. 1-5)

Referring to FIG. 1, operator-controlled assembly 13 of catheter assembly 10 is maintained exteriorly of the body of the patient. A proximal end of first tube 15 is suitably secured within a bore 25 defined in a housing 26. An inlet passage 27 is defined in the housing in axial alignment with an annular passage 28 (FIG. 2) defined between guide wire 14 and tube 15 to selectively communicate a suitably pressurized medicinal liquid, blood plasma or the like therethrough and/or to monitor the level of blood pressure.

A second housing 29 rotatably mounts a tubular shaft and connector 30 thereon and has a drain passage 31 adapted for connection to a vacuum source. The passage is constantly maintained in fluid communication with an annular passage 32, defined between tube 15 and a bore 33 formed axially through the center of shaft 30 and further defined between tubes 15 and 16 (FIG. 2). A distal end of passage 32 is closed and sealed by an O-ring 34, mounted between tube 15 and shaft 30, and a pair of axially spaced O-rings 35 are mounted between housing 29 and shaft 30. A snap ring 36 and a washer 37 retain the distal end of shaft 30 in a fixed axial position, relative to the housing.

Drive assembly 18, adapted to sequentially rotate shaft 30, second tube 16 and thus inner cutting head 19 of cutting means 17, comprises a third housing 40 rotatably mounting a worm gear 41 and a drive shaft 42 for the gear therein. The shaft has a standard drive connection 43 adapted to be coupled to a conventional motorized drive input (not shown) for rotating the shaft and worm gear in a controlled manner. The worm gear meshes with an output 44 that is keyed at 45 to shaft 30. A snap ring 46 and washer 47 retain the proximal end of shaft 30 in a fixed position relative to housing 40. As shown, a proximal end of tube 16 is adhesively bonded or otherwise suitably secured within bore 33 whereby the tube will provide a drive input to inner cutting head 19 of cutting means 17.

A fourth housing 50 functions as a rotary joint and fluid connector for supplying the above mentioned oxygen enriched fluid (e.g., blood plasma) to cutting means 17 and strainer cup 21. In particular, an inlet passage 51 is defined in housing 50 to communicate with an annular passage 52, defined between a tubular connector 53 mounted on housing 50 and tube 16. A pair of axially spaced O-ring seals 54 are mounted between housing 50 and connector 53 to seal-off passages 51 and 52 and an O-ring seal 55 is mounted between the connector and tube 16 to seal-off the proximal end of passage 52. The connector is held in a fixed axial position, relative to housing 50, by a snap ring 56 and a washer 57 and an annular shoulder 58 formed on the connector.

A flexible third tube 60 has a proximal end thereof secured on a tapered down end of connector 53 by a ring or band clamp 61. It can thus be understood from the above description that manipulation of housing 26, connector 30 (and attached housings 29, 40), and housing 50 will individually control the movements of tubes 15, 16 and 60, respectively.

Tube 60, as well as tubes 15 and 16, may comprise a standard smooth surface, medium to high density polyethylene or other suitable plastic material used in conventional biomedical devices. The distal end of tube 60 is adhesively bonded in a tubular guide sleeve 62 which thus forms a fixed extension of the tube. As shown in FIG. 2, when the catheter is in its retracted condition of operation for either insertion into or removal from a patient, component parts of the catheter are substantially housed in a protected position within guide sleeve 62. A collapsible frusto-conically shaped entrance seal 63 is reciprocally mounted within a distal end of guide sleeve 62 to seal-off the downstream side (relative to the heart) of the coronary artery from the aorta, as generally depicted at imaginary plane 64 in FIG. 1.

Entrance seal 63 is suitably secured on an annular mounting sleeve 65, reciprocally mounted on a pilot sleeve 66. A pair of longitudinally extending and diametrically opposed guide slots 67 are formed internally on guide sleeve 62 to slidably mount radially extending guide lugs 68, formed integrally on annular mounting sleeve 65, therein. As shown in FIG. 2, when pilot sleeve 66 is retracted within guide sleeve 62 in response to retraction of tube 15, entrance seal will collapse and will be retracted within the guide sleeve by its engagement with an annular shoulder 69 formed on the distal end of pilot sleeve 66. The entrance seal is composed of a thin walled silicone or other highly flexible plastic material approved for medical uses of this type that will permit the frusto-conically shaped seal to collapse and fold radially inwardly to facilitate such retraction.

A compression coil spring 70 is mounted within guide sleeve 62, axially between tube 60 and an end of sleeve 66, to bias pilot sleeve 66 rightwardly to its extended position, illustrated in FIG. 1. Passage 52, defined between tubes 16 and 60, communicates with an annular passage 71 defined between tube 16 and pilot sleeve 66 to communicate the above-mentioned oxygen enriched fluid over cutting means 17 to supply the fluid to the heart and to flush-out the fragments of the blockage severed by the cutting means. A vacuum is drawn at drain passage 31, defined in housing 29, so that the fragment-laden fluid is drained through the catheter via passage 32, defined between tubes 15 and 16.

As shown in FIG. 4, the outer surface of tube 15 is formed with a triangular configuration from approximately the point whereat the tube enters guide sleeve 62 to the distal end thereof whereat guide wire 14 projects forwardly therefrom. A mounting sleeve 72, having straining cup 21 suitably secured thereon, has an internal triangular configuration conforming to the outer configuration of tube 15. The mounting sleeve is adhesively bonded to tube 15 whereby the strainer cup will reciprocate with the tube. Outer cutting head 20 is slidably mounted on tube 15 by an integral mounting sleeve 73 that is internally configured triangularly (FIG. 4) to match the outer configuration of tube 15 whereby the outer cutting head can reciprocate on the tube, but cannot rotate relative thereto.

As shown in FIG. 3, inner cutter head 19 has a plurality of diagonal slots 74 formed therethrough to define a plurality of circumferentially spaced cutting blades 75 on cantilevered elements thereof. Likewise, outer cutting head 20 has a plurality of diagonal slots 76 formed therethrough to define a plurality of circumferentially spaced cutting blades 77. Blades 75 and 77 cross-over each other during the cutting action and each blade is preferably disposed at an acute angle relative to a longitudinal and rotational axis x of cutting means 17 and tube with the blades being disposed to define an included acute angle therebetween, preferably selected from the approximate range of from 10° to 20°. The cantilevered elements of the inner cutting head are sufficiently resilient and flexible to permit the outer cutting head to "snap-on" the inner cutting head when they are assembled together.

Straining cup 21 is preferably composed of a porous plastic material having a porosity in the range of 50 microns, for example. A typical plastic material for this purpose may constitute the Interflo ® porous plastic material manufactured by Chromex Corp. of Brooklyn, NY which has a porosity controllable within the range of from 10 to 150 microns and exhibits 10%–60% in void volume whereby flow control and filtration can be accurately maintained. Likewise, mounting sleeve 72 and the portion of tube 15 extending on the downstream side of cutting means 17 (towards strainer cup 21) can be formed of a porous plastic material of this type to continuously ensure the desired amount of oxygen to the heart.

Guide wire 14 may constitute a standard Teflon (polytelrafluroethylene) coated steel wire having a diameter in the approximate range of from 0.89 mm to 0.97 mm. The distal portion of the wire, approximately from cutting means 17 (FIG. 1) to the distal end of the wire, can be finely coiled in a conventional manner. The remaining portion of the wire is fabricated to be normally straight and uncoiled.

As schematically shown in FIG. 5, the center C of outer cutting head 20 can be mounted eccentrically on tube 15 and relative to longitudinal and normal rotational axis x of tube 15. For example, for an outer cutting he ad having an outside diameter of 3.0 mm and an eccentricity of 1.0 mm, the effective cutting diameter of cutting means 17 becomes 5.0 mm. Thus, the cutting head can be inserted into an artery to favor one side thereof and effectively cut-out blockages on the other side of the artery. Inner cutting head 19 will, of course, follow the position of the outer cutting head due to the inherent flexibility of tube 16. It should be understood that the outer diameter of the cutting means, whether concentric or eccentric, will depend on the surgical procedure and sizes of the blood vessels and blockages under consideration.

METHOD OF OPERATION (FIGS. 1-5)

Catheter 11 is inserted percutaneously into the aorta of a patient in its retracted condition illustrated in FIG. 2. The distal end of tube 15 can be frusto-conically shaped to facilitate such insertion. Prior to insertion of the catheter through skin 12 of the patient, an oxygen-enriched fluid, such as a suitably composed blood plasma or an oxygen enriched flurocarbon, is pumped within a normal blood pressure range from inlet 51 (FIG. 1) through passages 52, 71, slots 14 and passage 32 to evacuate any air in the catheter back to outlet or drain 31.

Guide wire 14 is used as a probe to guide the catheter to the blockage in the coronary artery of the patient with conventional x-ray or fluroscopy techniques being utilized to detect bands of magnetic material 22. When the artery is located, tubes 15 and 16 are suitably reciprocated to permit spring 70 to expand the catheter to its FIG. 1 extended position and to properly position strainer cup 21 and entrance seal 63 at the upstream and downstream sides of the blockage, respectively. The straining cup 21, now positioned to seal-off the downstream side of the coronary artery, is constructed to a sufficiently thin and flexible plastic material to enable it to expand-out to its FIG. 1 sealing condition against the inner wall of the coronary artery.

Once straining cup 21 and entrance seal 63 are precisely positioned in the coronary artery upon manipulation and reciprocation of tubes 15, 16 and 60, the operative procedure can commence. The entrance seal now seals-off the upstream side of the coronary artery from the aorta and, along with strainer cup and seal 21, will prevent fragments of the thereinafter cut-up blockage from regressing into the patients aorta or progressing into the heart proper.

Housings 29 and 40 and thus tube 16 are then moved in a controlled manner to extend cutting means 17, relative to pilot sleeve 66, into gradual cutting engagement with the blockage. It is contemplated that shaft 42 of drive assembly 18 will be rotated at speeds in the approximate range of from 10 rpm to 60 rpm under control of the operator to efficiently cut the blockage into fragments. Simultaneously therewith, the oxygen-enriched fluid, is being continuously communicated under a normal blood pressure range to inlet passage 51 to housing 50 and thence through passages 52 and 71 to the cutting means.

The fluid will pass thrugh slots 74 and 76 of the cutting means to flush-out the fragments and return the fragment-laden fluid back through drain passage 31, via passage 32 defined between tubes 15 and 16, under influence of the partial vacuum drawn at passage 31. Any residue fragments will be captured and retained within cup 21 and the catheter proper, upon retraction of tube 15 and the catheter to its FIG. 2 condition and removal of the catheter from the patient's body. The cut fragments collect naturally within the inner cutting head 19 and are retained therein with the aid of the pressurized fluid.

As described above, the oxygen-enriched fluid communicated to the coronary artery from inlet passage 51 will have a portion thereof pass through the straining cup to supply the coronary artery and heart with sufficient oxygen at an appropriate pressure to maintain it in a healthy condition. Passage 51, as well as passage 27 defined in housing 26, can be used to inject any necessary type of medicinal fluid to the contrary artery, if so desired. Also, passage 27 and its communicating passage 28 can also be utilized to monitor the blood pressure of the patient. Passages 28 and 32 are clearly shown in FIG. 2, but are obscure in FIG. 1 due to the reduced scale of this drawings Figure.

DETAILED DESCRIPTION (FIGS. 6 and 7)

FIGS. 6 and 7 illustrate an alternate catheter embodiment 11' wherein identical numerals depict corresponding construction and components but wherein numerals appearing in FIGS. 6 and 7 are accompanied by a prime symbol ('). Catheter 11' is also adapted to be incorporated into the type of operator-controlled assembly 13 illustrated in FIG. 1. The catheter also includes a flexible guide wire 14' that is rotatably and reciprocally mounted in the catheter to guide the catheter through the aorta for purposes of locating a coronary artery in the manner described above.

A flexible first tube 15', having the guide wire mounted therein to project from a distal end thereof, is mounted in a flexible second tube 16'. A cutting means 17' is adapted to engage and cut a blockage in a coronary artery into fragments in response to rotation of second tube 16' in much the same manner as described above in respect to the operation of cutting means 17. Tubes 15' and 16' are adapted to rotate relative to each other and cannot reciprocate relative to each other, in contrast to tubes 15 and 16 which are adapted for both relative rotary and reciprocal movements.

Cutting means 17' also comprises a generally spherically-shaped inner or male cutting head 19' secured on a distal end of second tube 16' for simultaneous rotation therewith and a spherically-shaped outer or female cutting head 20' suitably secured on first tube 15' at a mounting sleeve 73' thereof. The cutting heads are also constructed with overlying slots 74, 76 and blades 75, 77 in the manner illustrated in FIG. 3. In the manner described above, the overlying blades will function to engage and cut a blockage in an artery into fragments in much the same manner that a rotary type razor functions to shave a man's whiskers.

It should be understood that spaced bands of a standard magnetic material, such as material 22 shown in FIG. 2, can be suitably formed at strategic locations on the FIG. 6 catheter whereby precise location of the bands and cutting means 17', relative to a blockage in a coronary artery, can be readily detected by conventional x-ray equipment or fluroscopy techniques. It should be noted in FIG. 6 that strainer cup and seal 21, as well as entrance seal 63, have been omitted. A flexible third tube 60', corresponding to tube 60 in FIG. 2, is extended define an annular passage 52' around second tube 16'. Tube 60' is open at its distal end and sized to also provide a protective housing for cutting means 17' when it is retracted to its FIG. 6 condition for either insertion into or removal from a patient. It should be noted that tubes 15' and 16' and cutting heads 19' and 20' will reciprocate as a unit.

Passage 52' is adapted to communicate an oxygen-enriched fluid over cutting means 17' to flush-out the fragments of the blockage, severed by the cutting means, in much the same manner as described above. As further described above, a vacuum (or partial vacuum) can be drawn in an annular passage 32', corresponding to passage 32, so that the fragment-laden fluid is drained back to drain passage 31 (FIG. 1). A plurality of ports 78 may be formed through tube 60 to aid in supplying an oxygen enriched fluid, such as blood plasma, to an artery.

In addition to or in lieu of utilizing the vacuum drawn in passage in 32' to drain the fragment-laden fluid away from cutting means 17', a mechanical conveying means in the form of screw threads 79 and 80 could be used for this purpose. In particular, the conveying means is defined between tubes 15' and 16' for moving the fragments away from the cutting means and through passage 32' in response to rotation of tube 16'. In particular, first tube 15' has spiral left hand threads 79 formed on the outer surface thereof whereas second tube 16' has spiral right hand threads 80 formed internally thereon. Thus, rotation of second tube 16' during the cutting process will include movement and flow of the fragment-laden fluid leftwardly through passage 32' in FIGS. 6 and 7 and to drain 31 (FIG. 1).

As described above, each tube 15', 16' and 60' may comprise a standard medium to high density polyethelyne or other suitable plastic material used in conventional biomedical devices. As shown in FIG. 7, threads 80 may be formed internally on tube 16' by encapsulating a spiraled wire with the cured plastic by use of conventional molding techniques. Threads 79 are formed in a like manner. The threads may be formed throughout the entire lengths of tubes 15' and 16' and may each have a constant pitch or varied pitch, depending on the dictates of specific applications of this invention.

FIGS. 6 and 7 illustrate threads 79 and 80 as being generally of the "knuckle" type. However, other types (and combinations) could be used, such as a conventional Square, Acme, American National, American Standard, Sharp "V", Whitworth B&S Worm, Buttress or Dardelet thread. The threads can be of the single or multiple type with the specific design criteria (major and minor diameters, pitch, lead, crest, root, depth of thread, etc.) being selected to meet each specific application of the invention.

Catheter 11' is utilized on a patient in substantially the same manner as described above in respect to the use of catheter 11. Further, the center of outer cutting head 20' can be mounted eccentrically on tube 15' in the same manner as described above in reference to FIG. 5.

I claim:
1. An intravascular catheter for clearing a blockage in a blood vessel or the like comprising
   a flexible first tube,
   flexible guide means movably mounted within said first tube for locating said vessel,
   a rotary flexible second tube rotatable relative to said first tube and having said first tube mounted therein to define a passage therebetween,
   cutting means for cutting said blockage into fragments in response to continuous rotation of said second tube, and
   conveying means defined between said first and second tubes for mechanically inducing and moving said fragments away from said cutting means and through said passage in response to continuous rotation of said second tube relative to said first tube.

2. The catheter of claim 1 wherein said guide means comprises an elongated and flexible wire reciprocally and rotatably mounted within first said tube and defining an annular passage therebetween.

3. The catheter of claim 1 wherein said conveying means comprises a spiral thread formed on at least one of an outer surface of said first tube or an inner surface of said second tube.

4. The catheter of claim 3 wherein said conveying means comprises a left hand spiral thread formed on the outer surface of said first tube and a right hand spiral thread formed on the inner surface of said second tube to face the thread formed on the outer surface of said first tube.

5. The catheter of claim 4 wherein each of said threads comprise a spiral wire encapsulated by a plastic material composing a relative one of said first and second tubes.

6. The catheter of claim 4 wherein each of said threads extend substantially throughout the entire length of a respective one of first and second tubes and has a substantially uniform pitch.

7. The catheter of claim 1 further comprising a flexible third tube having said first and second tubes mounted therein and an annular passage defined between said second and third tubes that is open at its distal end and sized to receive said cutting means therein in response to retraction of said second tube relative to said third tube.

8. The catheter of claim 7 wherein said cutting means comprises an outer cutting head secured on said first tube, an inner cutting head secured on a distal end of said second tube for simultaneous rotation therewith and disposed in protected relationship within said outer cutting head and cooperating blade means formed on said inner and outer cutting heads for cutting said blockage into fragments.

9. The catheter of claim 8 wherein said blade means define a plurality of slots through each of said inner and outer cutting heads for communicating the passage defined between said second and third tubes with the passage defined between said first and second tubes.

10. The catheter of claim 8 wherein each of said inner and outer cutting heads are at least generally spherically shaped.

11. An intravascular catheter for clearing a blockage in a blood vessel or the like comprising a flexible first tube, a rotary flexible second tube rotatable relative to said first tube and having said first tube mounted therein to define a passage therebetween, and rotary cutting means for engaging and cutting said blockage into fragments including an outer cutting head secured on said first tube, an inner cutting head secured on said second tube for simultaneous rotation therewith and rotatably mounted in protected relationship within said outer cutting head, cooperating blade means formed on each of such inner and outer cutting heads for cutting said blockage into fragments in response to rotation of said second tube and, conveying means defined between said first and second tubes and responsive to relative rotation therebetween for mechanically inducing and conveying said fragments away from said cutting means and through said passage.

12. The catheter of claim 11 further comprising flexible guide means movably mounted in said first tube for locating said vessel.

13. The catheter of claim 11 further comprising an elongated and flexible guide wire reciprocally and rotatably mounted within first said tube.

14. The catheter of claim 11 wherein said conveying means includes a spiral thread formed on at least one of an outer surface of said first tube and an inner surface of said second tube for moving said fragments away from said cutting means and through the passage defined between said first and second tubes in response to rotation of said second tube.

15. The catheter of claim 14 wherein said conveying means comprises a left hand spiral thread formed on the outer surface of said first tube and a right hand spiral thread formed on the inner surface of said second tube to face the thread formed on the outer surface of said first tube.

16. The catheter of claim 11 further comprising a flexible third tube having said first and second tubes mounted therein and an annular passage defined between said second and third tubes that is open at its distal end and sized to receive said cutting means therein in response to retraction of said second tube.

17. The catheter of claim 16 wherein said blade means define a plurality of slots through each of said inner and outer cutting heads for communicating the passage defined between said second and third tubes with a passage defined between said first and second tubes.

18. The catheter of claim 11 wherein each of said inner and outer cutting heads are at least generally spherically shaped.

* * * * *